United States Patent
Harder et al.

(10) Patent No.: US 11,684,519 B2
(45) Date of Patent: Jun. 27, 2023

(54) MEDICAL DRESSING TO TREAT SUCKING CHEST WOUND

(71) Applicant: SAFEGUARD MEDICAL HOLDCO, LLC, Harrisburg, NC (US)

(72) Inventors: Paul X. Harder, Williamsburg, VA (US); Jeffrey B. Gray, Indianapolis, IN (US); John Biddle, Monticello, IN (US)

(73) Assignee: SAFEGUARD MEDICAL HOLDCO, LLC, Harrisburg, NC (US)

( * ) Notice: Subject to any disclaimer, the term of this patent is extended or adjusted under 35 U.S.C. 154(b) by 286 days.

(21) Appl. No.: 17/146,151

(22) Filed: Jan. 11, 2021

(65) Prior Publication Data

US 2022/0218533 A1  Jul. 14, 2022

(51) Int. Cl.
*A61F 13/00* (2006.01)
*A61F 13/02* (2006.01)
(Continued)

(52) U.S. Cl.
CPC ........ *A61F 13/143* (2013.01); *A61F 13/0289* (2013.01); *B29C 65/08* (2013.01);
(Continued)

(58) Field of Classification Search
CPC .... A61F 13/143; A61F 2/82; A61F 13/00068; A61F 2002/30677; A61F 2210/0076; A61F 2250/0009; A61F 2/0059; A61F 2/07; A61F 2/16; A61F 2/2412; A61F 2/32; A61F 2/3859; A61F 2/3877; A61F 2/389; A61F 2/44; A61F 5/0123; A61F 5/055; A61F 13/00021; A61F 13/00063; A61F 13/0206;
(Continued)

(56) References Cited

U.S. PATENT DOCUMENTS

| 4,371,686 A | 2/1983 | Yamamoto et al. |
| 4,465,062 A | 8/1984 | Versaggi et al. |

(Continued)

FOREIGN PATENT DOCUMENTS

WO     2021/097400 A1     5/2021

OTHER PUBLICATIONS

"Hyfin Vent Chest Seal—Individual", https://www.narescue.com/all-products/hyfin-vent-chest-seal.html (Mar. 2017), 3 pages.
(Continued)

*Primary Examiner* — Ellen S Hock
(74) *Attorney, Agent, or Firm* — Corner Counsel, LLC

(57) ABSTRACT

A medical dressing including: a flexible base layer including a front surface configured to face a skin of a patient and a back surface opposite the front surface, wherein the flexible base layer includes a first opening; an adhesive layer on the front surface of the base layer; a flexible cover layer entirely covering the opening of the base layer; a flexible intermediate layer sandwiched between the base layer and the cover layer, wherein the base layer, cover layer and intermediate layer joined together along an annular pattern extending entirely around the first and second openings, wherein the annular pattern joints the base layer to the intermediate layer entirely around the first and second openings, and the annular pattern joins the layers around the first and second openings except at slots extending beyond an outer edge of the cover layer and ending before an outer edge of the intermediate layer.

20 Claims, 5 Drawing Sheets

(51) Int. Cl.
    *A61F 17/00*         (2006.01)
    *A61F 13/14*         (2006.01)
    *B29C 65/08*         (2006.01)
    *B29C 65/00*         (2006.01)
    *B32B 7/12*          (2006.01)
    *B32B 7/06*          (2019.01)
    *B32B 27/08*         (2006.01)
    *B32B 27/40*         (2006.01)
    *B32B 3/26*          (2006.01)

(52) U.S. Cl.
    CPC .......... *B29C 66/8145* (2013.01); *B32B 3/266* (2013.01); *B32B 7/06* (2013.01); *B32B 7/12* (2013.01); *B32B 27/08* (2013.01); *B32B 27/40* (2013.01); *A61F 2013/00251* (2013.01); *B32B 2307/732* (2013.01); *B32B 2405/00* (2013.01); *B32B 2535/00* (2013.01); *Y10T 428/24322* (2015.01)

(58) Field of Classification Search
    CPC ...... A61F 13/023; A61F 13/126; A61F 13/42; A61F 2002/043; A61F 2002/9528; A61F 2013/00476; A61F 2210/009; A61F 2230/0071; A61F 2250/0059; A61F 2/013; A61F 2/04
    See application file for complete search history.

(56) References Cited

U.S. PATENT DOCUMENTS

| | | |
|---|---|---|
| 4,717,382 A | 1/1988 | Clemens et al. |
| 5,106,362 A | 4/1992 | Gilman |
| 5,195,977 A | 3/1993 | Pollitt |
| 5,431,633 A | 7/1995 | Fury |
| 5,478,333 A | 12/1995 | Asherman, Jr. |
| 5,603,946 A | 2/1997 | Constantine |
| 7,429,687 B2 | 9/2008 | Kauth et al. |
| 7,504,549 B2 | 3/2009 | Castellani et al. |
| 8,309,786 B2 | 11/2012 | Scheremet et al. |
| 8,710,289 B2 | 4/2014 | Russell et al. |
| 9,000,251 B2 | 4/2015 | Murphy et al. |
| D766,448 S | 9/2016 | Gergely et al. |
| 9,452,088 B2 | 9/2016 | Shulman et al. |
| 9,549,840 B2 | 1/2017 | Buus |
| 10,383,988 B2 | 8/2019 | Bussett |
| 10,639,207 B1 | 5/2020 | Harder et al. |
| 10,660,994 B2 | 5/2020 | Askem et al. |
| D898,925 S | 10/2020 | Kelbie et al. |
| 2001/0031370 A1 | 10/2001 | Kundel |
| 2003/0204174 A1 | 10/2003 | Cisko, Jr. |
| 2007/0232978 A1 | 10/2007 | Castellani |
| 2007/0244421 A1 | 10/2007 | Graham |
| 2008/0091152 A1 | 4/2008 | Asherman |
| 2010/0054340 A1 | 3/2010 | Reibman |
| 2012/0046582 A1 | 2/2012 | Hopman et al. |
| 2012/0078153 A1 | 3/2012 | Russell et al. |
| 2015/0320919 A1 | 11/2015 | Bussett et al. |
| 2017/0312402 A1 | 11/2017 | McDonald |

OTHER PUBLICATIONS

Ronald Bergman, Ph.D., "Sucking Chest Wound", Anatomy Atlases, www.anatomyatlases.org, Mar. 24, 2017, 5 pages.
"Bolin Chest Seal", H&H Medical, Dec. 20, 2020, 6 pages.
Hyfin Vent Chest Seal Twin Pack, www.chinookmed.com (Mar. 24, 2017), 6 pages.

MEDICAL DRESSING TO TREAT SUCKING CHEST WOUND

TECHNICAL FIELD

This invention relates to a medical dressing for treating open chest injuries or other injuries that may expose the pleural space or chest cavity.

BACKGROUND

Chest trauma, including piercing or penetrating chest wounds, can occur as the result of an accidental or deliberate penetration of a foreign object into the body. Risk from chest trauma can be exacerbated if the internal chest volume or lungs are exposed to the external environment, such that atmospheric air enters the internal chest volume. Air entering the chest volume can cause the collapse of the lung(s) in the chest volume. Effective triage of a piercing or penetrating chest wound can be achieved with specifically adapted medical dressings which prevent atmospheric air entering the internal chest volume and thereby reduce the risk of a collapsed lung, also referred to as a pneumothorax.

The lungs are made up of layers of tissue known as pleura and are maintained within an enclosed pleural space. The pleural space is in the internal chest volume and is naturally maintained at a slight, negative pressure as compared to atmospheric pressure. The negative pressure aids in the expansion of the lung during an inhalation of a breath.

When an individual suffers a puncture wound to the chest, the wound may penetrate the chest cavity and expose the pleural space to atmospheric air and thus atmospheric air pressure. Atmospheric air will tend to flow through the puncture wound into the pleura space due to the natural below atmospheric pressure in the pleura space. Because the flow of air through the wound and into the pleural space is typically audible, these types of wounds are commonly referred to as "sucking chest wounds."

If atmospheric air is allowed to flow through the wound into the pleura space, the increased pressure in the pleura space may precipitate a pneumothorax, e.g., a lung collapse. A pneumothorax results from the abnormal buildup of air pressure in the pleural space and may manifest as an uncoupling of the lung from the chest wall. Immediate symptoms typically include a sudden onset of sharp chest pain (general one-sided and localized to the side of the wound opening, and shortness of breath. If left untreated, these symptoms may progress to difficulty breathing, or even death.

Generally, the prescribed treatment to a penetrating chest wound, e.g., a sucking chest wound, is to limit air entry into the pleura space by sealing the wound and evacuate air from the pleura space.

Conventional chest wound dressings include the medical dressing disclosed in U.S. Pat. No. 10,639,207, which is formed of a base layer and a cover layer fused directly to the base layer to cover an opening in the base layer. One-way air channels are formed between the base and cover layers to allow air to escape from a chest wound and prevent air entering the chest wound.

BRIEF DESCRIPTION

A need developed for a chest wound dressing formed of three or more layers fused together. However, forming air channels between two layers in a dressing creates when there are three or more layers in the dressing. Forming air channels between two layers and fusing all layers appeared to preclude fusing all layers in one fusing step. But, multiple fusing steps would be costly and time consuming. A need arose for a chest wound dressing formed of three or more layers that could be formed by fusing the layers together in a single fusing step, wherein air channels are formed between at least two of the layers.

The invention may be embodied as a medical dressing comprising: a flexible base layer including a front surface configured to face a skin of a patient and a back surface opposite the front surface, wherein the flexible base layer includes a first opening; an adhesive layer on the front surface of the base layer wherein the adhesive layer extends entirely around the opening; a flexible cover layer entirely covering the opening of the base layer; a flexible intermediate layer sandwiched between the base layer and the cover layer, wherein the intermediate layer includes a second opening aligned with the first opening; the base layer, cover layer and intermediate layer joined together along an annular pattern extending entirely around the first and second openings, wherein the annular pattern joints the base layer to the intermediate layer entirely around the first and second openings, and the annular pattern joins the cover layer, intermediate layer and base layer around the first and second openings except at slots extending beyond an outer edge of the cover layer and ending before an outer edge of the intermediate layer.

The invention may be embodied as a medical dressing comprising: a flexible base layer including a front surface configured to face a skin of a patient and a back surface opposite the front surface, wherein the flexible base layer includes a first opening; an adhesive layer on the front surface of the base layer wherein the adhesive layer extends entirely around the opening; a flexible cover layer entirely covering the opening of the base layer and overlapping at least a portion of the main membrane; a flexible intermediate layer sandwiched between the base layer and the cover layer, wherein the intermediate layer includes a second opening aligned with the first opening; and a pattern joining the base layer and intermediate layer entirely around the first and second openings and the pattern joins the cover layer, intermediate layer and base layer around the first and second openings except at slots extending beyond an outer edge of the cover layer and ending before an outer edge of the intermediate layer.

The invention may be embodied as a method to form a medical dressing comprising: overlaying a cover layer on an intermediate layer and the intermediate layer on a base layer such that openings in the intermediate and base layers are aligned and the cover layer overlays the openings; fusing together the cover layer, the intermediate layer and the base layer by applying an annular welding tool face to at least one of the cover layer and base layer and applying welding energy to the template, wherein the annular tool face extends entirely around the first and second openings and fuses the base layer to the intermediate layer entirely around the first and second openings and fuses the cover layer, intermediate layer and base layer around the first and second openings except slots extend beyond an outer edge of the cover layer and end before an outer edge of the intermediate layer, and applying an adhesive layer on a side the base layer opposite to the intermediate layer, wherein the adhesive layer extends entirely around the opening.

DETAILED DESCRIPTION

Figure 1:
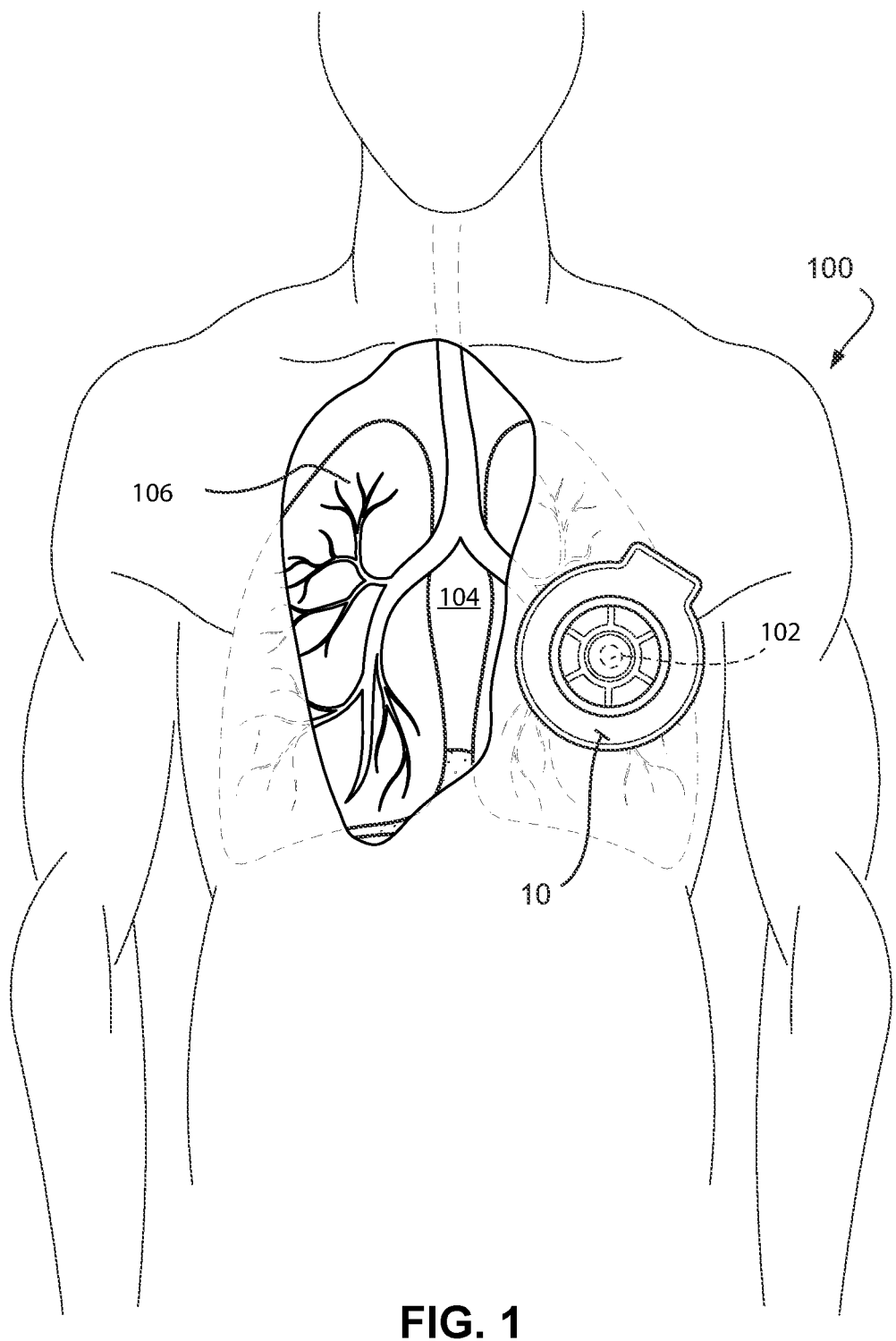
FIG. 1 is a view of a patient with a medical dressing applied to the lower chest or abdomen.

FIG. 1 shows a patient 100 with a chest wound, such as a puncture 102 that extends through the chest wall. The puncture 102 may allow air to flows from the atmosphere into the pleural space 104. The air entering the pleural space can increase the pressure in the space and thereby collapse the lung(s) 106. Immediate and emergency treatment of the chest wound involves the application of a dressing that allows excess air in the pleural space to vent to the atmosphere and prevents additional air from being drawn back into the pleura space.

A medical dressing 10 is applied to the chest puncture 102. The dressing is applied such that the puncture 102 is aligned with the center of the dressing 10. Before the dressing is applied, the wound may be cleaned by removing blood and dirt from the skin surround the wound. An adhesive layer on one side of the dressing seals the dressing to the skin. The dressing covers the puncture 102 to prevent water, dirt and other material from entering the wound. The dressing may also assist in stopping further loss of blood from the wound. The dressing also prevents air from being drawn into the puncture 102 while also allowing air to vent from the puncture and to the atmosphere. A second medical dressing 10 may be applied to the back (not shown) of the patient where there may be an exit (or entrance) wound, especially if the wound is caused by a gunshot.

Figure 2:
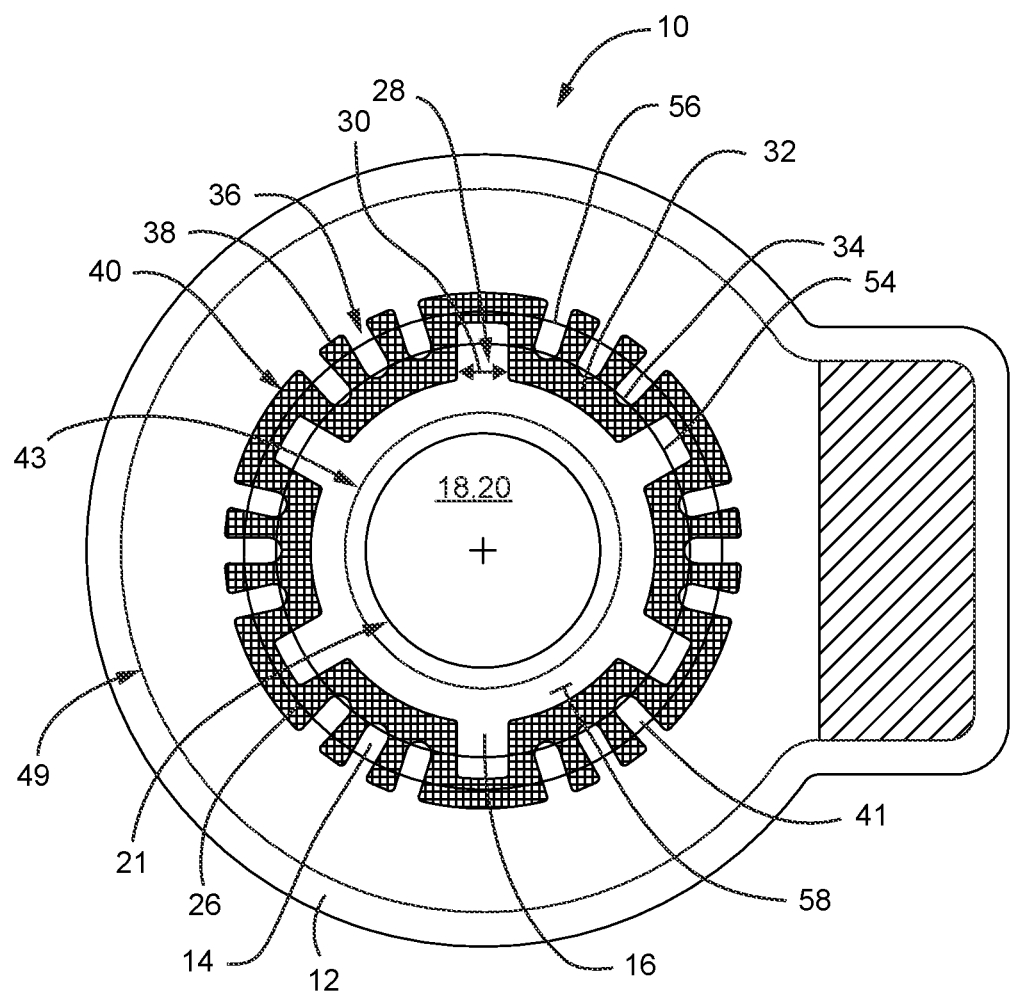
FIG. 2 is a top view of the medical dressing.
Figure 3:
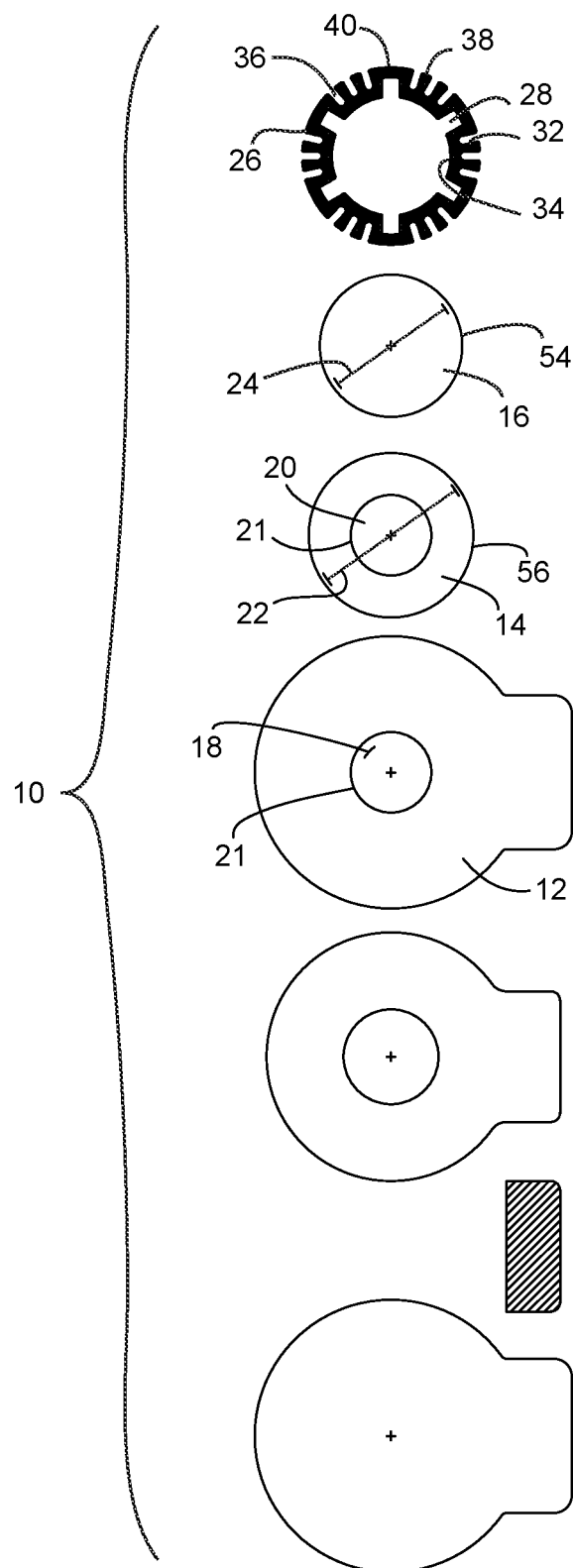
FIG. 3 is an exploded view of the medical dressing showing the layers of the dressing.

FIG. 2 shows a top view of the medical dressing 10, and FIG. 3 shows an exploded view of the layers of the medical dressing 10.

The principal layers of the medical dressing 10 are a base layer 12, an annular intermediate layer(s) 14 and a circular disc cover layer 16. Each of these principal layers may be formed of a polyurethane (PU) sheet having a thickness of 10 mils to 5 mils. The base layer member 12 may be thicker, such as by a factor of two, than each of the intermediate and cover layers. The intermediate layer may have the same thickness and the cover layer, or may be thicker than the cover layer if additional firmness is needed to support the cover layer.

The circular disc cover layer 16 is the upper layer of the dressing 10, the base layer 12 is the bottom layer and the intermediate layer(s) 14 are sandwiched between the disc cover layer and the bottom layer. The cover layer 16 is a continuous circular sheet that forms a gas impermeable cover over a center opening 18 of the base layer. The cover layer prevents gas, liquids and solids from entering the puncture wound 102 through the openings 18, 20 in the base and intermediate layers.

The opening 18 in the base layer may be circular, oval, curvilinear in shape, rectangular or have some other shape. The diameter or other dimension from one side of the opening 18 to the other may be one inch, one and one-half inches, two inches, two and one-half inches or other diameter selected to extend around the wound or anticipated wound dimensions. The opening 18 should be centered on the wound 102 when the dressing 10 is applied to the skin on the chest of the patient. The opening 18 may have an area sufficiently greater than the puncture so that the edges of the puncture are not coated with the adhesive of the dressing. The opening 18 allows air in the pleura space to vent from the wound and through the opening.

The cover layer 16 overlaps and covers the opening 18 in the base layer. The cover layer 16, intermediate layer 14 and base layer 12 are fused together such that atmospheric air cannot pass through the layers and that air from the wound can vent through air channels described below. The cover, intermediate and base layers may be transparent or translucent to allow the wound and skin below the dressing 10 to be viewed while the dressing is applied to the skin.

The intermediate layer 14 includes an opening 20 which may have the same diameter or dimensions as the diameter or dimensions of the opening 18 in the base layer. The inner edges 21 of the intermediate layer 14 and base layer 12 form the perimeter of the openings 18, 20.

The outer diameter 22 of the intermediate layer 14 may be in a range of three to four inches, e.g., 3.5 inch. The outer diameter 24 of the cover layer 16 may be in a range of 2.5 inch to 3.5 inch. The diameter 24 of the cover layer is smaller than the diameter 22 of the intermediate layer 14 by, for example, one half of an inch or in range of 12 to 17 percent less than the outside diameter 22 of the intermediate layer.

The circular disc cover layer 16, intermediate layer(s) 14 and the base layer 12 are fused together along a fusing template 26 that defines the regions of the layers that are fused. Several different methods of fusion may be used to fuse the layers 12, 14 and 16. One method of fusing the layers is by welding, e.g., fusing, the layers together with energy such as heat, radio frequencies (RF), other electromagnetic frequencies, and ultrasonic pressure frequencies, such as frequencies in a range of 10 to 100 MHz. The fused areas are permanent and highly durable. The fusion creates molecular bonds, e.g., fusion, between the layers 12, 14, 16.

The intermediate layer(s) 14 provide added thickness, strength and firmness to an annular region surrounding the opening 18 in the base layer. The cover layer 16 may be thin and flexible to easily deform, e.g., move up and down, due to a pressure difference between atmospheric pressure and the pressure of the puncture wound, e.g., the pressure in the pleural space. As the cover layer deflects upward due to air being pushed out of the puncture wound, the cover layer 16 pulls on the intermediate layer 14. The intermediate layer 14 distributes the force applied by the cover layer to the base layer 12 to a larger area than only the annular overlap between the cover layer and the base layer. This distribution of force over the larger area of the intermediate layer reduces the concentration of force applied to the base layer and the adhesive between the base layer and the skin around the wound. Reducing the concentration of forces applied to the base layer and adhesive, reduces the tendency of the adhesive to pull away from the skin and form unwanted air channels between the adhesive and the skin.

Fusing the layers is performed simultaneously on all of the layers 12, 14 and 16. This one step fusing reduces time and costs in forming the medical dressing 10. The fusion step simultaneously joins the circular disc cover layer 16 to the intermediate layer 14 and the intermediate layer 14 to the base layer 12. If there are multiple intermediate layers, the one step of fusion will also join these intermediate layers together. The energy provided by the fusion tool is sufficient to fuse the layers 12, 14 and 16 together are the locations on the layers corresponding to the welding tool.

A fusion template 26, e.g., heating template, defines the locations where the layers 12, 14, 16 are fused together by a heating element or other tool that fuses the layers together in the area defined by the template. The template 26 is a pattern which illustrates the areas of the layers that are fused together. All of the layers 12, 14 and 16 are fused together at the areas of the template 26. The template 26 may be an annular pattern arranged to fuse the layers together and provide air channels 28 between the cover layer 16 and the intermediate layer 14. To provide for the air channels 28, the template 26 has slots 30 so that energy is not applied to the portion of the layers which form the air channels and thus the layers are not fused in the area corresponding to the slots 30.

The template 26 includes a generally annular first region 32 that overlaps the cover layer 16 and extends radially outward to just short of the outer diameter 24 cover layer 16. The outer radial edge 34 of the first region may be at or about 1/16 inch inward of the outer edge 54 of the cover layer 16. The first region 32 may have a width of in a range of 1/16 to 1/10 of the diameter 24 of the cover layer 16. The first region 32 seals the layers 12, 14 and 16 together in a contiguous annular ring interrupted by the slots 30. The first region 34 may be sufficient to fuse the layers together such that the regions of the template radially outward of the first region are optional.

The template 26 may also have a generally annular second region 36, which is optional. The second region includes fingers 38 which extend in a radial direction out from the first region. The second region seals the intermediate later to the base layer 12 at regions radially aligned with the slots 30. The fingers extend over the intermediate layers to fuse the intermediate layers to the base layer. The fingers seal the inner later to the base layer in an annular region of the intermediate layer that is radially beyond the cover layer.

The second region also includes bridges 40 which are regions radially aligned with the slots 40 and the bridges extend transverse to a radial line across the slot. The bridges 40 seal the inner layer to the base layer to prevent air channels 28 formed by the slots 30 and between the intermediate layer 14 and the base layer 12. The bridges are optional. Without the bridges, air channels could be formed between the intermediate and base layers, as well as between the cover layer and the intermediate layer. Gaps 41 in the template are between adjacent fingers or between a finger and an adjacent bride. The fingers 38 and bridges 40 secure the intermediate layer to the base layer at regions between these layers that are radially outward of the outer circumference of the cover layer 16. Thus, the fingers and bridges assist in distributing radially outward the force between the cover and intermediate layers due to air being vented from the puncture wound.

The fingers 38 may have uniform dimensions and shapes such that all fingers have the same shape and size. The fingers may have a substantially rectangular shape when viewed from above, except that the sides of each finger may be aligned along racial lines and thus diverge slightly as the finger extends radially outward. The length along a radial direction of each finger may be in a range of 0.3 to 0.5 inch. Each finger 38 may have radially inward end that mergers with the first annular region 32 of the template 26 and be substantially aligned with the outer edge 54 of the cover layer. Each finger may extend from the outer edge 54 of the cover layer over the intermediate layer, and a short distance, e.g., 0.1 to 0.2 inch, past the outer edge 56 of the intermediate layer. Each finger may have a width in an arc direction of 0.2 to 0.25 inch at its greatest width. The width of each finger may increase 20% to 40% in a radial direction along its length.

The bridges 40 may each have a width in an arc direction in a range of 1.0 to 1.4 inch and a length of 0.3 to 0.5 inch, which is substantially the same length as the fingers. The width of the slot 30 in each bridge may be 0.25 to 0.5 inch. The slot extends radially entirely through the inner annular ring 46 and beyond the edge 54 of the cover layer to 0.5 to 0.8% of the radial distance between the edge of the cover layer and the edge 56 of the inner layer. This distance may be in a range of 0.15 to 0.25 inch. Further, there may be two or three fingers for each bridge and slot arrangement. The ratio of length to width of the slots may be selected to balance the needs to prevent air or blood entering the wound through the channel, allowing air and blood to vent from the wound and reducing the risk that the air channel becomes clogged with blood or other material. A ratio length to width in a range of 2 to 8, such as 4, may be optimal for balancing these needs.

The air channels 28 each define air passages extending between the cover layer 16 and the intermediate layer 14 that exhausts to the atmosphere at the outer edge 54 of the cover layer. The air channels 28 have a radially inward entrance at an annular region 58 between the cover and intermediate layers, and radially inward of the welded area corresponding to the template 26.

When gases and liquid, e.g., air and blood, flow out of the wound and into the gap between the skin and the cover layer, the pressure of these gases and liquids is greater than atmospheric air. This pressure deforms the cover layer away from the skin which opens the annular region 58 and the air channels 28 to allow the gasses and liquids to flow away from the wound and out through the dressing 10. When the pressure between the wound and the cover layer drops, atmospheric pressure pushes the cover layer against the intermediate layer and closes the air channels 28 and the annular region 58.

The number of air channels 28 may be five, six or more. Because of the large number of air channels, one or more of the air channels may clog, such as with blood, while other air channels continue to expand and allow venting of air from the chest wound. The width and length of each air channel, such as the radial length of the slot 30, may be selected to be sufficiently long and narrow to ensure that the passage collapses and prevents air conveyance when the air pressure at the wound is at or below atmospheric pressure. A competing and contrary requirement is that the air channel should be short and wide to avoid being clogged with blood and debris and to air readily vent from the wound with minimal resistance due to the air channel. Balancing these competing requirements is preferred to achieve an optimal air channel.

Figure 4:
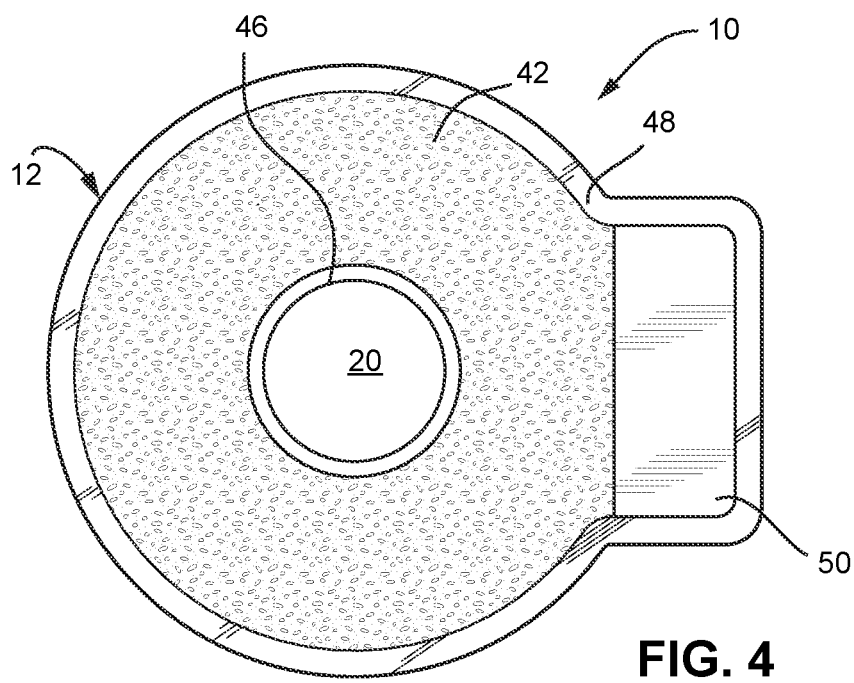
FIG. 4 is a bottom view of the medical dressing.
Figure 5:
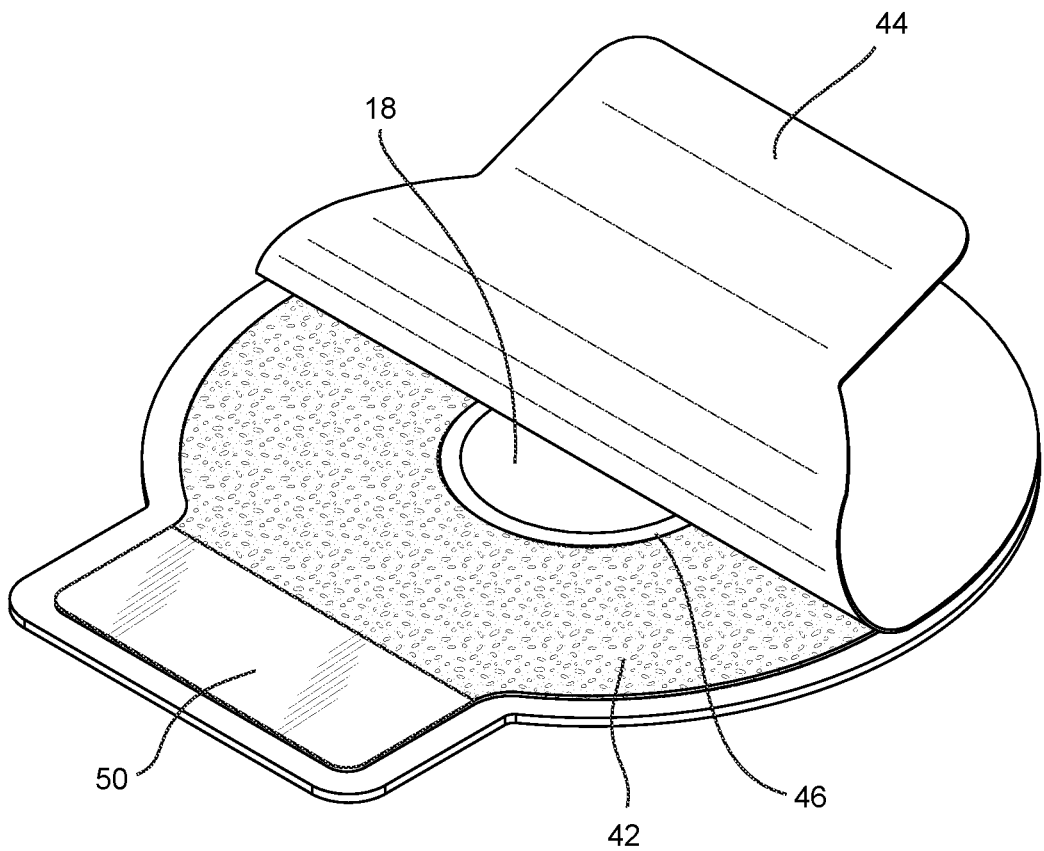
FIG. 5 is a perspective view of the bottom of the medical dressing, showing the release liner partially peeled from the base layer.

As shown in FIGS. 4 and 5, the front surface (skin side) of the base layer 12 is configured to face a chest of a patient. The back surface of the base layer is opposite the front surface and is fused to the intermediate layer 14. The front surface is substantially coated in its entirety with an adhesive layer 42. The adhesive layer includes an outer edge 43 and an inner edge 45. The inner edge is radially outward of the inner edges 19 of the base layer and the intermediate layer due to an annular ring 46 on the front surface of the base layer.

The adhesive layer 42 may be a biocompatible adhesive disposed for securing the dressing 10 to a patient's skin. Suitable adhesives for adhering the flange body to the patient's skin include hydro gel, acrylic, silicone gel, silicone PSA or hydrocolloid. The adhesive layer 42 may include a substrate layer that is coated on both sides with adhesives. The substrate provides support for the adhesives.

A release liner (membrane) 44 covers the adhesive layer 42 until the medical dressing 10 is to be applied to the skin of the chest. Immediately before the medical dressing 10 is applied to the skin, the release liner 44 is peeled from the dressing adhesive layer 42. The exposed adhesive layer and the rest of the medical dressing are applied to the skin as the dressing is pressed to the skin. The dressing is applied such that the opening 18 is centered on the wound 102.

An inner annular ring 46 on the front surface of the base layer is devoid of adhesive and extends from the outer perimeter of the opening 18 to the inner edge 43 of the adhesive layer 42. The inner annular ring 46 assists in preventing adhesive from creeping around the edge of the opening 18 and between the cover layer 16 and intermediate layer 14. Such adhesive creep could seal one or more of the air channels 28. The inner annular ring 46 may have a width (from the opening to the adhesive layer) of one-eighth of an inch to one-quarter of an inch. The annular inner ring is a region of the base layer, but alternatively may be a structural ring having minimal height, e.g., less than one-eighth of an inch.

An outer annular ring 48 on the front surface (skin side) of the base layer 12 is also devoid of adhesive 42. The outer annular ring extends from the outer edge 49 of the adhesive layer 42 to the outer wedge of the base layer 12. The outer annular ring may have a width of 0.3 to 0.7 of an inch, such as 0.5 inch. The annular perimeter region may assist in preventing adhesive from creeping from between the intermediate layer and the cover layer, and limits contact between the adhesive and potential contaminants that may be present around the application area. The outer annular ring 48 also facilitates dressing 10 removal by providing a lip that can be grasped to pull the dressing off the skin.

A rectangular tab 50 on the front side of the base layer main and the adhesive layer provides a grip for removing the medical dressing from the skin. A back surface of the tab 50 may adhere to the adhesive layer, and the front side may be a non-adhesive coating or layer that does not adhere to the skin or to the release liner 44.

Figure 6:
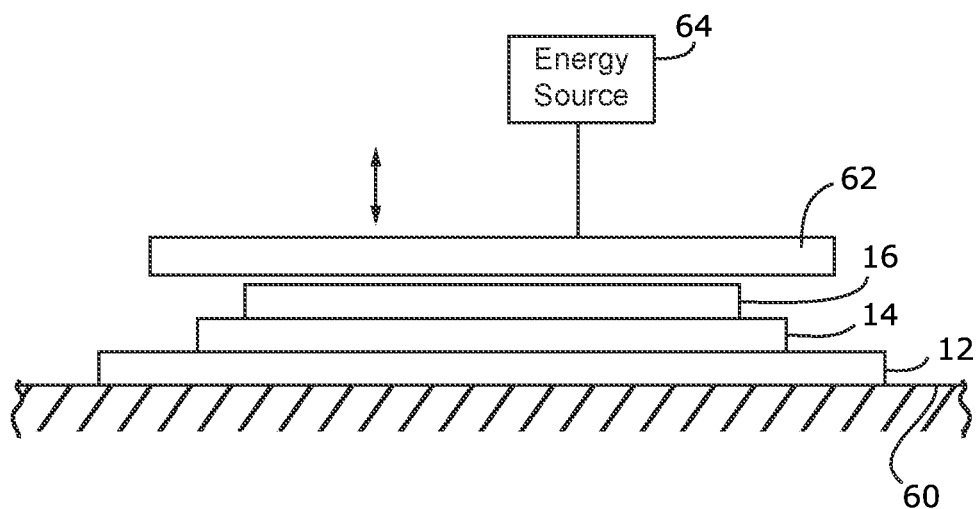
FIG. 6 illustrates a method for fusing the base, intermediate and cover layers.

FIG. 6 illustrates a manufacturing process for fusing, e.g., welding, together the base layer 12, the intermediate layer 14 and the cover layer 16. These layers are assembled by placing the base layer on a flat substrate 60, e.g. metal table. The intermediate layer is laid on the base layer and the cover layer is laid on the intermediate layer. Alternatively, the base, intermediate and cover layers may be placed as an assembly on the substrate 60. The layers 12, 14, 16, are brought together such that the openings 18 and 20 of the based and intermediate layers are aligned, and the cover layer is centered on these openings. A heating or ultrasonic tool 62 moves towards the layers and presses the layers between the tool and the substrate. A front surface of the tool in contact with the layers, e.g., the cover layer, has a shape corresponding to the template 26. A source of heat or ultrasonic energy 64 applies the energy to the front surface of the tool to cause the layers to be fused together at the areas corresponding to the template. Alternatively, other types of energy may be applied to the layers, such as radio frequencies welding and laser through-transmission welding, or other modes of welding such as chemical adhesives may be used to join the base, intermediate and cover layers in the designed pattern.

After the layers are fused together, the adhesive layer 42 may be applied to the side of the base layer not facing the intermediate layer. The release liner 44 is applied to the adhesive layer, if not already applied when the adhesive layer is applied to the base layer, to complete the wound dressing 10. The completed wound dressing 10 may be enclosed in a package, such as an airtight package, for safe keeping until the wound dressing is needed to treat a wound.

While at least one exemplary embodiment of the present invention(s) is disclosed herein, it should be understood that modifications, substitutions and alternatives may be apparent to one of ordinary skill in the art and can be made without departing from the scope of this disclosure. This disclosure is intended to cover any adaptations or variations of the exemplary embodiment(s). In addition, in this disclosure, the terms "comprise" or "comprising" do not exclude other elements or steps, the terms "a" or "one" do not exclude a plural number, and the term "or" means either or both. Furthermore, characteristics or steps which have been described may also be used in combination with other characteristics or steps and in any order unless the disclosure or context suggests otherwise. This disclosure hereby incorporates by reference the complete disclosure of any patent or application from which it claims benefit or priority.

The invention is:

1. A medical dressing comprising:
   a flexible base layer including a front surface configured to face a skin of a patient and a back surface opposite the front surface, wherein the flexible base layer includes a first opening;
   an adhesive layer on the front surface of the base layer wherein the adhesive layer extends entirely around the first opening;
   a flexible cover layer entirely covering the opening of the base layer; and
   a flexible intermediate layer sandwiched between the base layer and the cover layer, wherein the intermediate layer includes a second opening aligned with the first opening;
   wherein the base layer, cover layer and intermediate layer are joined together along an annular pattern extending entirely around the first and second openings, wherein the annular pattern joints the base layer to the intermediate layer entirely around the first and second openings, and the annular pattern joins the cover layer, intermediate layer and base layer around the first and second openings except at slots extending beyond an outer edge of the cover layer and ending before an outer edge of the intermediate layer.

2. The medical dressing of claim 1, wherein the slots correspond to air channels between the cover layer and the intermediate layer.

3. The medical dressing of claim 2, wherein the air channels extend radially from the first and second openings and are arranged symmetrically around the opening.

4. The medical dressing of claim 1, wherein the annular pattern includes bridges each defining a radially outward end to a respective one of the slots and the bridges are aligned with the outer edge of the intermediate layer.

5. The medical dressing of claim 4, wherein the annular pattern includes fingers extending radially outward from the outer edge of the cover layer and to at least the outer edge of the intermediate layer.

6. The medical dressing of claim 5, wherein each of the fingers is adjacent another one of the fingers and is adjacent one of the slots.

7. The medical dressing of claim 1, wherein the annular pattern includes a first annular region radially inward of the outer edge of the cover layer and the slots extend radially through the first annular region, wherein the second annular region extends from the outer edge of the cover layer to at least the outer edge of the intermediate layer, wherein the second annular region includes bridges extending in an arc direction across each of the slots.

8. The medical dressing of claim 7, wherein the second annular region includes fingers each extending in a radial direction from the outer edge of the cover layer to at least the outer edge of the intermediate layer.

9. The medical dressing of claim 6, wherein the fingers are each separated by gaps in the annular pattern from other ones of the fingers and from the bridges.

10. The medical dressing of claim 1, wherein the cover layer is a circular disc, the intermediate layer is an annular ring, and the first and second openings are each circular.

11. The medical dressing of claim 1, wherein the intermediate layer is a plurality of intermediate layers.

12. A medical dressing comprising:
   a flexible base layer including a front surface configured to face a skin of a patient and a back surface opposite the front surface, wherein the flexible base layer includes a first opening;
   an adhesive layer on the front surface of the base layer wherein the adhesive layer extends entirely around the opening;
   a flexible cover layer entirely covering the opening of the base layer;
   a flexible intermediate layer sandwiched between the base layer and the cover layer, wherein the intermediate layer includes a second opening aligned with the first opening; and
   an annular pattern joining the base layer and intermediate layer entirely around the first and second openings and the pattern joins the cover layer, intermediate layer and base layer around the first and second openings except at slots extending beyond an outer edge of the cover layer and ending before an outer edge of the intermediate layer.

13. The medical dressing of claim 12, wherein the slots correspond to air channels between the cover layer and the intermediate layer.

14. The medical dressing of claim 12, wherein the annular pattern includes bridges each defining a radially outward end to a respective one of the slots and the bridges are aligned with the outer edge of the intermediate layer.

15. The medical dressing of claim 13, wherein the air channels extend radially from the first and second openings and are arranged symmetrically around the opening.

16. The medical dressing of claim 14, wherein the annular pattern includes fingers extending radially outward from the outer edge of the cover layer and to at least the outer edge of the intermediate layer.

17. The medical dressing of claim 12, wherein the annular pattern includes a first annular region radially inward of the outer edge of the cover layer and the slots extend radially through the first annular region, wherein the second annular region extends from the outer edge of the cover layer to at least the outer edge of the intermediate layer, wherein the second annular region includes bridges extending in an arc direction across each of the slots.

18. The medical dressing of claim 17, wherein the second annular region includes fingers each extending in a radial direction from the outer edge of the cover layer to at least the outer edge of the intermediate layer.

19. The medical dressing of claim 12, wherein the cover layer is a circular disc, the intermediate layer is an annular ring, and the first and second openings are each circular.

20. The medical dressing of claim 12, wherein the intermediate layer is a plurality of intermediate layers.

* * * * *